United States Patent [19]

Shay

[11] Patent Number: 4,865,447
[45] Date of Patent: Sep. 12, 1989

[54] CONTAINER INSPECTION APPARATUS HAVING EACH OUTPUT DEMODULATED AT A SPECIFIC SOURCE FREQUENCY

[75] Inventor: Timothy W. Shay, Horseheads, N.Y.

[73] Assignee: Emhart Industries, Inc., Indianapolis, Ind.

[21] Appl. No.: 211,119

[22] Filed: Jun. 21, 1988

Related U.S. Application Data

[63] Continuation of Ser. No. 914,709, Oct. 2, 1986, abandoned.

[51] Int. Cl.$^4$ ............................................. G01N 21/90
[52] U.S. Cl. ................................. 356/240; 250/223 B
[58] Field of Search ............................. 356/240, 428; 250/223 B

[56] References Cited

U.S. PATENT DOCUMENTS

| | | | |
|---|---|---|---|
| 3,851,975 | 12/1974 | Serret | 356/428 |
| 3,894,806 | 7/1975 | Remy et al. | 356/240 |
| 4,165,227 | 8/1979 | Frewin | 356/240 |
| 4,213,042 | 7/1980 | Beach et al. | 250/223 B |
| 4,265,545 | 5/1981 | Slaker | 356/431 |
| 4,672,200 | 6/1987 | Claypool et al. | 250/223 B |

Primary Examiner—Vincent P. McGraw
Assistant Examiner—S. A. Turner
Attorney, Agent, or Firm—Carl A. Forest

[57] ABSTRACT

Glassware inspection apparatus comprises a first light emitting diode position to illuminate a first region of the ware, a first driver for driving the first light emitting diode in a first modulated mode, a first photodetector positioned for receiving light of the first light emitting diode which illuminates the first region of the container, and a first demodulator for the output of the first photodetector. The apparatus also comprises a second light emitting diode positioned to illuminate a second region of the container, a driver for driving the second light emitting diode in a second modulated mode, a second photodetector positioned for receiving light of the second light emitting diode which illuminates the second region of the container, and a second demodulator for the output of the second photodetector. The two modulation modes minimize cross-talk between the first and second light emitting diodes.

19 Claims, 3 Drawing Sheets

CONTAINER INSPECTION APPARATUS HAVING EACH OUTPUT DEMODULATED AT A SPECIFIC SOURCE FREQUENCY

This is a continuation of co-pending application Ser. No. 914,709 filed on Oct. 2, 1986 abandoned.

BACKGROUND OF THE INVENTION

The invention relates generally to apparatus and processes for inspecting containers and other objects and deals more particularly with apparatus and processes for optically detecting flaws in and other features of such objects.

Flaws in glassware may take the form of checks, and three common types of checks are vertical splits, horizontal ring checks and horizontal thread checks. Often the checks occur in the finish portion of the glassware, and are objectionable because they seriously weaken the glassware and lead to fractures.

A previously known apparatus for detecting such checks comprises a plurality of incandescent lamps, each of which directing light to a different, localized portion of the container finish, and a plurality of optical sensors positioned to receive the light of associated ones of the incandescent lamps after reflection from a check. The incandescent lamps and sensors are supported at an inspection site at which the containers are rotated to expose each check in the finish portion to illumination by at least one of the incandescent lamps and viewing by at least one of the sensors.

Because the shape and location of each check cannot be accurately predicted, the incandescent lamps and sensors are positioned experimentally to detect checks in test containers. During such experiments, first the incandescent lamp is positioned to project light toward a checked finish region at a previously determined angle relative to the horizontal. Then, the test container is rotated and an operator visually determine an angle at which a check in the container reflects light from the associated incandescent lamp. Finally, an optical sensor is positioned along this reflective angle. This procedure is repeated for each pair of incandescent lamp and associated optical sensor. It should be noted that the visible nature of the light from the incandescent lamp facilitates the set-up procedure.

While this system has proven effective, some difficulties have been experienced in providing an adequate signal to noise ratio for the light reflected from the checks because the light emitted by the incandescent lamps is qualitatively indistinguishable from ambient light. Also, there have been some difficulties with cross-talk because light from each incandescent lamp may occasionally reflect to the optical sensor of another incandescent lamp. If such reflections result from illumination of a non-defective region of a container, then a non-defective bottle may be deemed defective and later rejected.

U.S. Pat. No. 3,851,975 to Serret discloses inspection apparatus comprising an incandescent lamp, a mechanical modulating disk located between the incandescent lamp and a container, a plurality of optical sensors and a plurality of electronic receivers connected to the optical sensors. The modulating disk comprises a plurality of groups of orifices, the orifices of each group being evenly spaced and concentrically located about the disk axis. Light from the incandescent lamp passes through each group of orifices and is chopped to form a pulsing illumination pattern. The number and spacing of orifices of each group are different than the number and spacing of the orifices of the other groups so that the light passing through each group has a different pulsing frequency than the light of the other groups. Each receiver is tuned to the frequency of the emitted light of an associated optical sensor. Consequently, the light modulated by each group of orifices and reflected by the container can be distinguished from the light of the other orifices so that cross-talk is minimized. Such tuning also improves the signal to noise ratio. However, for some applications, the mechanical system of the 3,851,975 system may be too bulky and susceptible to vibrations which introduce other modulation frequencies.

Accordingly, a general object of the present invention is to provide inspection apparatus for detecting flaws in and other features of containers which apparatus provides a high signal to noise ratio, low degree of cross-talk, manageable size and lack of moving parts. A related process is also desired.

SUMMARY OF THE INVENTION

The invention resides in apparatus for inspecting a container for defects and other features. The apparatus comprises a first light emitting diode or other source positioned to illuminate a first region of said container, a first driver for driving the light emitting diode or other source in a first modulated mode, and a first photodetector or other sensor positioned for receiving light of the first source which illuminates the first region of the container. A first demodulator demodulates an output of the first photodetector to extract inspection information. The apparatus also comprises a second light emitting diode or other source of light positioned to illuminate a second region of the container, a second driver for driving the second light emitting diode or other source in a second modulated mode, and a second photodetector or other sensor positioned for receiving light of the second light source which illuminates the second region of the container. A second demodulator demodulates the output of the second photodetector so that cross-talk between the first and second light emitting diodes or other sources is minimized.

DETAILED DESCRIPTION OF THE PREFERRED EMBODIMENTS

Figure 1:
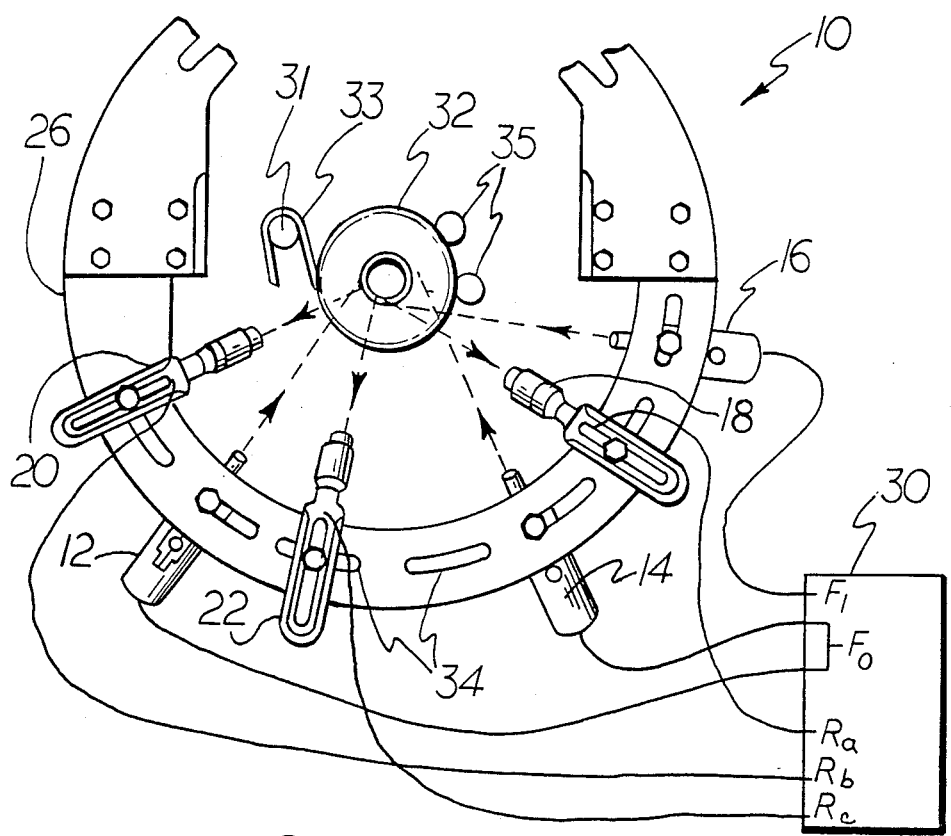
FIG. 1 is a top plan view of a container and inspection apparatus embodying the invention.

Turning now to the drawings, FIG. 1 illustrates inspection apparatus generally designated 10 in which the invention is embodied. The apparatus 10 comprises three light emitting diode units 12, 14 and 16, three photodetector diode units 18, 20 and 22 associated respectively with each of the light emitting diode units 12, 14 and 16, a bracket 26 for supporting the light emitting diode units and the photodetector diode units, and an electronic control 30 for driving high intensity, visible light emitting diodes within the respective units and processing signals provided by photodetector diodes within the respective units. Each of the light emitting diode units and photodetector diode units are trained on a finish portion of a glass container 32. By way of example, the light emitter/receptor pair 12, 18 scans for vertical splits, the light emitter/receptor pair 14, 20 scans for ring checks and the light emitter/receptor pair 16, 22 scans for thread checks. Also by way of example, the photodetector diode unit of each pair is positioned at a substantial circumferential angle relative to the associated light emitting diode unit corresponding to a path of light reflected from a check.

Figure 2:
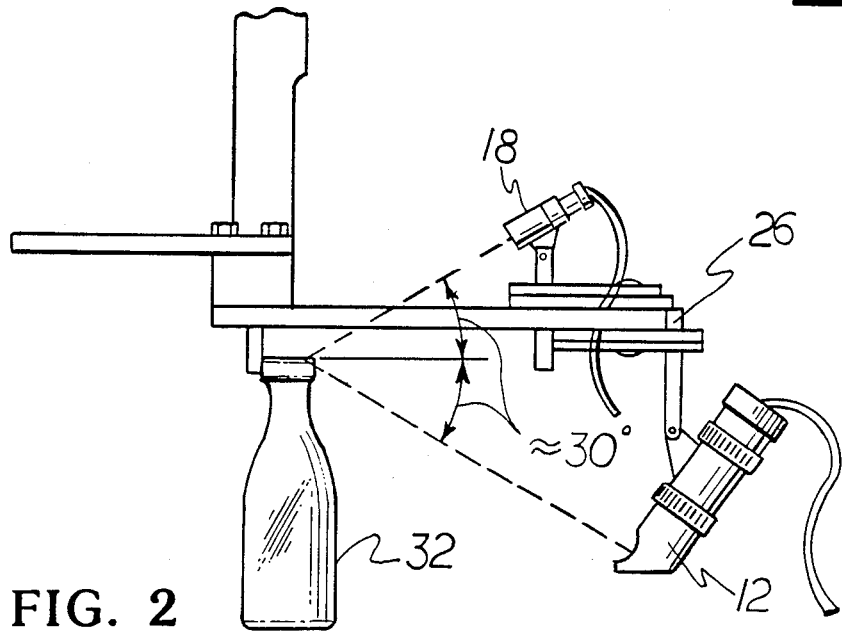
FIG. 2 is a side, plan view of the container and one emitter/receiver pair of the inspection apparatus of FIG. 1.

As illustrated in FIG. 2, the light emitting diode unit 12 is displaced from the associated photodetector diode unit 18 by a substantial angle in the vertical direction to correspond to the aforesaid path of reflected light. For example, the light emitting diode unit is supported to project light at an upward angle approximately 30° from the horizontal toward the container finish and the associated sensor 18 is supported to receive light projected from the container finish upwardly at an angle approximately 30° above the horizontal. While not shown in FIG. 2, the light emitting diode units and photodetector diode units of the other pairs 14, 20 and 16, 22 are similarly displaced vertically from one another.

During inspection, the container 32 is rotated by a pulley 31 and belt 33 acting against two wheels 35, 35.

Although not illustrated in the Figures, the exact positions of the light emitting diode units 12, 14 and 16 and photodetector diode units 18, 20 and 22 were determined experimentally. First, an operator positioned and activated each light emitting diode unit and then caused the container 32 to rotate slowly. Next, the operator visually determined an angle of reflectivity from the associated type of check by viewing through the sensor optics. Then, the operator positioned the photodetector diode unit along the angle of reflection. Slots 34 in the bracket 26 facilitate such precise positioning of the light emitting diode units and photodetector diode units.

Figure 3:
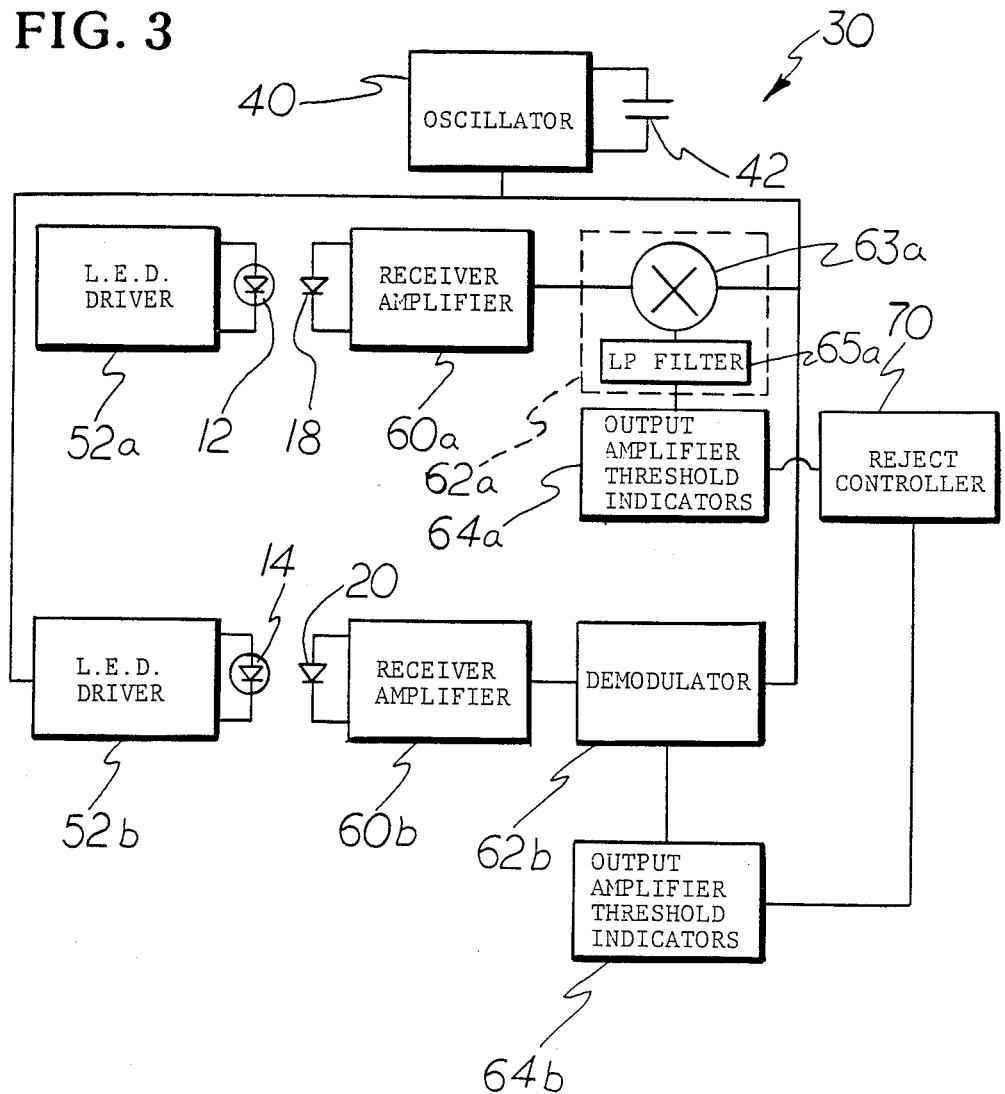
FIG. 3 is a block diagram of circuitry for two emitter/receiver pairs within an electronic control of the inspection apparatus of FIG. 1.
Figure 4:
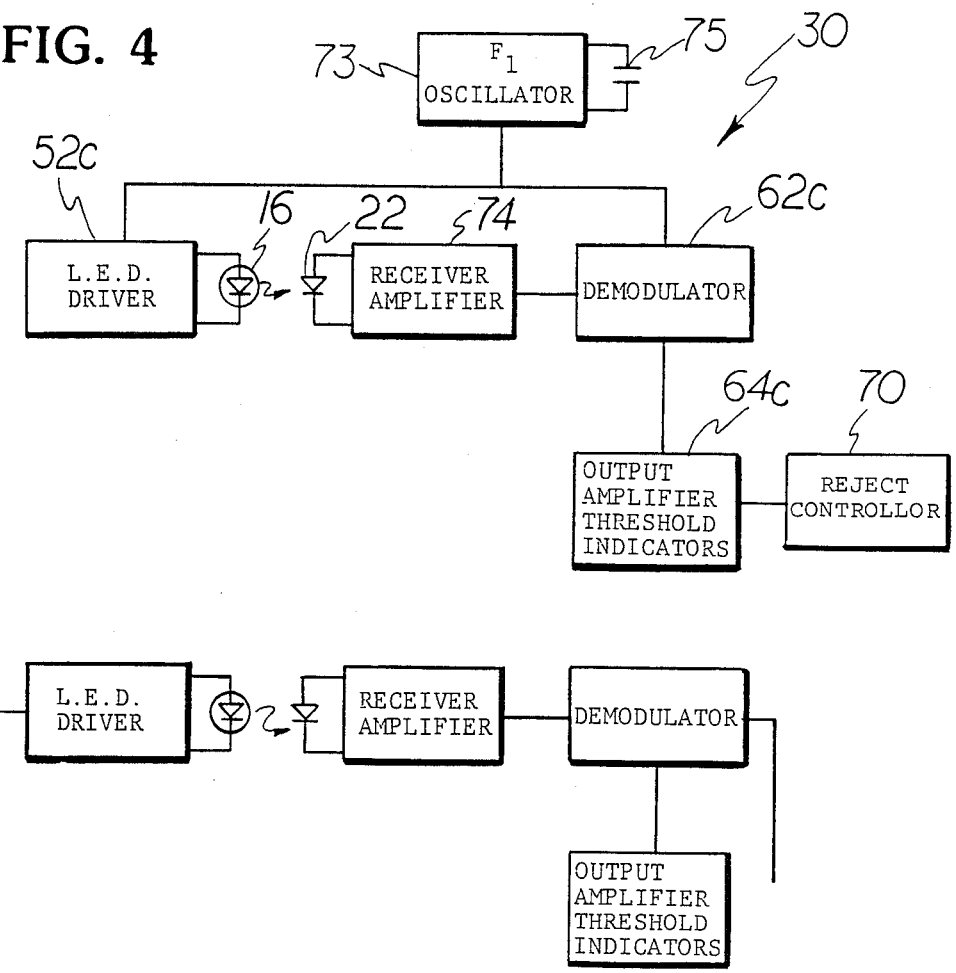
FIG. 4 is a block diagram of circuitry for another emitter/receiver pair within the electronic control of FIG 1.

Focusing now on the invention, FIGS. 3 and 4 schematically illustrate circuitry within the electronic control 30 which circuitry controls the light emitting diode units 12, 14 and 16 and the associated photodetector diode units 18, 20 and 22. As illustrated in FIG. 3, the electronic control 30 comprises an oscillator 40 having an external frequency controlling capacitor 42 for providing a sinusoidal wave form at frequency $F_0$. By way of example, the frequency of the oscillator 40 is 15 kilohertz. The oscillator 40 supplies the sinusoidal wave form to two identical current drivers 52a and 52b which square-up the sinusoidal wave form and drive the light emitting diode units 12 and 14, respectively. Consequently, the light emitting diode units 12 and 14 emit modulated light which pulses at the frequency $F_0$.

Figure 5:
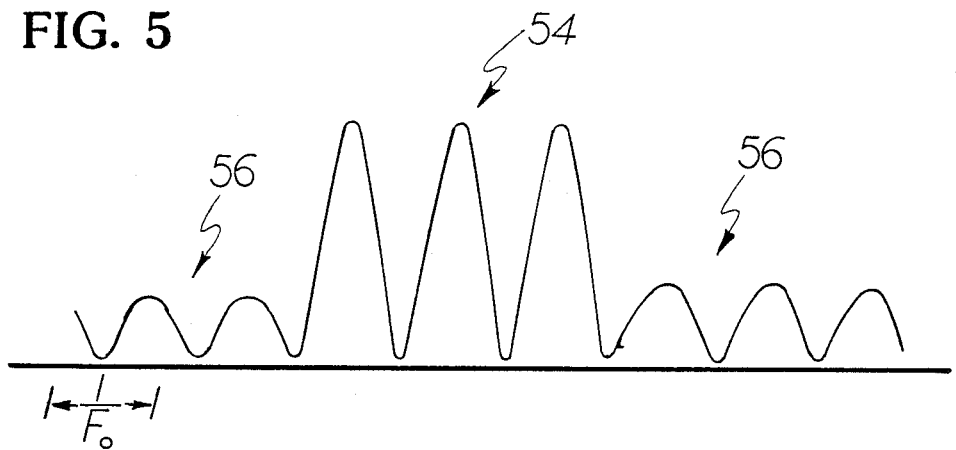
FIG. 5 illustrates light of one emitter which is reflected from the container of FIG. 1.

Light originally transmitted by the light emitting diode unit 12 and reflected from the container 32 toward the photodetector diode unit 18 is illustrated in FIG. 5 and causes the photodetector diode unit 18 to output a signal having a fundamental frequency equal to $F_0$. The output of the photodetector unit 18 due to this light also contains frequency components slightly above and below the fundamental frequency due to the rotation of the container 32 and the variation in the intensity of the reflected light as the vertical check passes through the field of the light emitter/receptor pair 12, 18. The output of the photodetector unit 18 also contains another fundamental frequency due to illumination by the light emitting diode unit 16 and reflections from the container 32 which are received by the photodetector unit 18.

A relatively high intensity portion of the FIG. 5 pattern is indicated generally by the numeral 54 and corresponds to reflections of the unit 12 light from the vertical split while relatively low intensity portions 56, 56 of the FIG. 5 pattern correspond to reflections of the unit 12 light from regions of the container 32 finish which do not contain a vertical check. The output of the photodetector diode unit 18 is supplied to a receiver 60a which amplifies the signal and optionally includes a pass band filter centered at the frequency $F_0$. The output of the receiver 60a is supplied to a demodulator 62a which, by way of example, comprises a multiplier 63a and a low pass filter 65a. The multiplier 63a has two inputs, one connected to the receiver 60a and the other connected to the output of the oscillator 40. The output of the multiplier 63a contains substantial energy in a first low frequency range close to that of the amplitude modulation caused by the rotation of the container 32, a second relatively high frequency range at approximately twice the frequency $F_0$, and third and fourth frequency ranges well above the first range due to the light of the light emitting diode unit 16 which is received by the photodetector unit 18. The output of the multiplier is passed through the low pass filter 65a to attenuate the relative high frequency components of the second, third and fourth ranges and thereby detect the relatively low frequency envelope of the first range of the multiplied signal. The envelope has a relatively high magnitude portion corresponding to the vertical split portion 54 and a relatively low magnitude portion corresponding to the normal portion 56, 56. Alternately, the demodulator 62a may comprise a phase lock loop circuit.

The output of the demodulator 62a is supplied to a threshold detector 64a to distinguish the relatively high magnitude envelope portion corresponding to the vertical check from the relatively low magnitude envelope portion corresponding to the non-checked portion of the finish. The threshold detector 64a optionally includes an amplifier for transmitting the output to a reject controller 70 which signals a rejector (not shown) to reject a container containing a vertical split.

Light originally transmitted by the light emitting diode unit 14 and reflected by a ring check toward the photodetector diode unit 20 is similarly processed by a receiver 60b, a demodulator 62b and a threshold detector 64b which components are identical to the respective receiver 60a, demodulator 62a and threshold detector 64a components described above. The output of the threshold detector 64b is also supplied to the reject controller 70 to indicate the presence of ring checks and to subsequently cause rejection of containers containing them.

The modulation or pulsing mode of operation of the light emitting diode units 12 and 14 and the utilization of the corresponding demodulation circuitry 62a and 62b improve the signal to noise ratio of the reflected light as compared to the signal to noise ratio of the incandescent lamp system described in the Background of the Invention because the demodulators 62a and 62b (and optional band pass filters within the receivers 60a and 60b) distinguish and attenuate signals corresponding to ambient light. It should be noted that because the light emitting diode units 12 and 14 operate at the same modulation or pulsing frequency, the frequency components of light emitted by the light emitting diode unit 12 cannot easily be distinguished from that of light emitted from the light emitting diode unit 14. However, in the illustrated example, such distinction is not necessary because of the relative positioning between the light emitting diode units 12 and 14 and the photodetector diode units 20 and 22. Little of the light emitted by the light emitting diode unit 12 is ever picked-up by the photodetector diode unit 20 and little of the light emitted by the light emitting diode unit 14 is ever picked up by the photodetector diode unit 18.

As illustrated in FIG. 4, the electronic control 30 also comprises an oscillator 73 having an external, frequency controlling capacitor 75. The oscillator 73 outputs a sinusoidal wave form having a frequency $F_1$ which, by way of example, is approximately 19 kilohertz. The optional 19 kilohertz is sufficiently separated from the optional 15 kilohertz of the oscillator 40 so that resultant signals produced by the associated photodetector units can be distinguished from each other by suitable low pass filters or other features of the associated demodulators. The output of the oscillator 73 is supplied to a current driver 52c which is identical to the drivers 52a and 52b and drives the light emitting diode unit 16. Light emitted by the unit 16 and reflected by a thread check toward the associated photodetector diode unit 22 causes the unit 22 to output a signal having a fundamental frequency equal to $F_1$ of the oscillator 73 and slightly lower and higher frequencies caused by the passing of the thread check through the field of the photodetector diode unit 22. The photodetector diode unit 16 also receives light at the other frequency, $F_0$, which light was originally emitted by the light emitting diode units 12 and 14. A receiver 74 amplifies the output of the photodetector diode unit 22 and optionally includes a band pass filter centered at the frequency $F_1$. The output of the receiver 74 is supplied to a demodulator 62c which detects the envelope of the amplifier 74 output signal which corresponds to the $F_1$ light emitted by the unit 16. By way of example, the demodulator 62c is similar to the demodulators 62a and 62b, and is adapted to detect an envelope of a signal having the fundamental frequency $F_1$. The output of the demodulator 62c is supplied to a threshold detector 64c which is similar to the threshold detectors 64a and 64b, and the output of the threshold detector 64c is also supplied to the reject controller 70.

The pulsing modulation of the light emitting diode unit 16 and the corresponding processing circuitry 74 and 62c which is tuned to the frequency $F_1$ improve the signal to noise ratio of the signal for reasons noted above. In addition and in accordance with an object of the invention, because the light emitting diode unit 16 and associated electronics operates at the frequency $F_1$ whereas the light emitting diode units 12 and 14 and associated electronics operate at the frequency $F_0$ and the frequency $F_1$ is substantially separated from the frequency $F_0$, cross-talk is minimized. That is, even though light emitted from either light emitting diode unit 12 or 14 may reflect from the container 32 toward the photodetector diode unit 22 or even be emitted directly toward the photodetector diode unit 22, electrical signals resulting from such light will be attenuated by the optional band pass filter within the receiver 74 and the demodulator 62c and therefore, such light will not be confused with light emitted by the light emitting diode unit 16 and reflected by a thread check toward the photodetector diode unit 22. Conversely, because the light emitting diode unit 16 emits light at the pulsing modulation frequency $F_1$ and demodulator 62a and 62b are tuned at $F_0$ (and optional receivers 60a and 60b are tuned at $F_0$), any of such light which is picked-up by either photodetector diode unit 18 or 20 is distinguishable from light emitted from the light emitting diode unit 16 and reflected by checks in the container finish.

It should also be noted that in accordance with other objects of the invention, the inspection apparatus requires no moving parts and is immune to vibrations.

By the foregoing, apparatus and processes for inspecting containers and other apparatus have been disclosed. However, numerous modifications and substitutions may be made without deviating from the scope of the invention. For example, if desired, one or more additional light emitter/receiver pairs may be provided to detect other defects in the container or other features such as the container profile. Such additional light emitter/receiver pair may be operated at a third frequency, for example 25 kilohertz, to avoid cross-talk.

Also, if desired, both the light emitting diode units 12 and 14 may be driven by the same driver 52a and the outputs of the respective photodetector diode units 60a and 60b may be supplied to the same receiver 60a. Alternately, if desired, the light emitter/receiver pair 14, 20 may be operated from a different oscillator than the oscillator 40 and at a different frequency than the oscillators 40 and 73 in the event that light emitted from the light emitting diode unit 12 is picked up by the photodetector diode unit 20 or light emitted from the light emitting diode unit 14 is picked up by the photodetector diode unit 18.

Also, if desired, more than one receiver can be used in conjunction with any single source as long as it is tuned to the same frequency as the source. This is useful if the same type of check reflects at a variety of angles.

Also, if desired, the light of the high intensity light emitting diode units may be aimed by optical fibers, and optical fibers used to pick-up the reflections. Also, the photodetector diode units may be operated in a transmission mode instead of a reflective mode to detect the blockage of light by certain types of container features. Therefore, the invention has been disclosed by way of illustration and not limitation and reference should be made to the following claims to determine the scope of the invention.

What is claimed:

1. Apparatus for inspecting a glass container, said apparatus comprising:

a first light emitting diode positioned to illuminate a first region of said container with visible light, first driver means for driving said first light emitting diode in a pulsed mode at a first fundamental frequency, first photodetector means positioned to receive light of said first light emitting diode which is reflected from a check in said first region, first receiver and demodulator means coupled to said first photodetector means and tuned to said first fundamental frequency for extracting inspection information from said first photodetector means, a second light emitting diode positioned to illuminate a second region of said container with visible light, second driver means for driving said second light emitting diode in a pulsed mode at a second fundamental frequency, second photodetector means positioned to receive light of said second light emitting diode which is reflected from a check in said second region, and second receiver and demodulator means coupled to said second photodetector means and tuned to said second fundamental frequency for extracting inspection information from said second photodetector means.

2. Apparatus as set forth in claim 1, further comprising:

a third light emitting diode positioned to illuminate a third region of said container with visible light, third means for driving said third light emitting diode in a pulsed mode at said first fundamental frequency, third photodetector means positioned to receive light of said third light emitting diode which is reflected from a check in said third region while avoiding light of said first light emitting diode, and third receiver and demodulator means coupled to said third photodetector means and tuned to said first fundamental frequency for extracting inspection information from said third photodetector means.

3. Apparatus as set forth in claim 1 further comprising means for causing the relative rotation of the container with respect to the first and second photodetector means and receiver and demodulator means.

4. Apparatus as set forth in claim 1 wherein the first and second regions are at the finish of said container.

5. Apparatus for inspecting a glass container, said apparatus comprising:

a first light emitting diode positioned to illuminate the first region of said container with visible light, first driver means for driving said first light emitting diode in a pulsed mode at a first fundamental frequency, first photodetector means positioned to receive light of said first light emitting diode which is reflected from a check receiver and demodulator means coupled to said first photodetector means and tuned to said first fundamental frequency for extracting inspection information from said first photodetector means, a second light emitting diode positioned to illuminate a second region of said container with visible light, second driver means for driving said second light emitting diode in a pulsed mode at a second fundamental frequency, second photodetector means positioned to receive light of said second light emitting diode which is reflected from a check in said second region, second receiver and demodulator means coupled to said second photodetector means and tuned to said second fundamental frequency for extracting inspection information from said second photodetector means, and means for causing the relative rotation of the container with respect to the first and second photodetector means and receiver and demodulator means.

6. Apparatus as set forth in claim 5, further comprising:

a third light emitting diode positioned to illuminate a third region of said container with visible light, third means for driving said third light emitting diode in a pulsed mode at said first fundamental frequency, third photodetector means positioned to receive light of said third light emitting diode which is reflected from a check in said third region while avoiding light of said first light emitting diode, and third receiver and demodulator means coupled to said third photodetector means and tuned to said first fundamental frequency for extracting inspection information from said third photodetector means.

7. Apparatus as defined in claim 5 wherein said first and second regions are at the finish of said container.

8. Apparatus for inspecting a glass container, said apparatus comprising:

a first light emitting diode positioned to illuminate the first region of said container with visible light, first driver means for driving said first light emitting diode in a pulsed mode at a first fundamental frequency, first photodetector means positioned to receive light of said first light emitting diode which is reflected from a check in said first region, first receiver and demodulator means coupled to said first photodetector means and tuned to said first fundamental frequency for extracting inspection information from said first photodetector means, said first receiver and demodulator means including a low pass filter, a second light emitting diode positioned to illuminate a second region of said container with visible light, second driver means for driving said second light emitting diode in a pulsed mode at a second fundamental frequency, second photodetector means positioned to receive light of said second light emitting diode which is reflected from a check in said second region, and second receiver and demodulator means coupled to said second photodetector means and tuned to said second fundamental frequency for extracting inspection information from said second photodetector means, said second receiver and demodulator means including a low pass filter.

9. Apparatus for inspecting a container, said apparatus comprising:

light source means for illuminating said container;

driver means for driving said light source at a predetermined frequency, photodetector means for receiving light from said light source means and providing a detector signal representative of said received light;

demodulator means responsive to said detector signal for demodulating said detector signal and providing a demodulated signal including inspection information.

10. Apparatus as in claim 9 wherein said demodulator means comprises a synchronous demodulator.

11. Apparatus as in claim 10 wherein said demodulator means further comprises a low pass filter.

12. Apparatus as in claim 9 wherein said predetermined frequency is greater than or equal to 14 kilohertz.

13. Apparatus as in claim 9 wherein said photodetector means comprises a photodetector diode electrically connected to a receiver amplifier circuit.

14. Apparatus as in claim 9 wherein:

said light source means comprises a first source of light positioned to illuminate a first region of said container and a second source of light positioned to illuminate a second region of said container;

said driver means comprises first driver means for driving said first source of light at a first frequency and second driver means for driving said second source of light at a second frequency different from said first frequency;

said photodetector means comprises first photodetector means positioned for receiving light of said first source which illuminates said first region of said container and second photodetector means positioned for receiving light of said second source which illuminates said second region of said container; and said demodulator means comprises first receiver and demodulator means coupled to said first photodetector means and tuned to said first frequency for extracting inspection information form said first photodetector means and second receiver and demodulator means coupled to said second photodetector means and tuned to said second frequency for extracting inspection information from said second photodetector means.

15. Apparatus as set forth in claim 14 wherein said first source of light comprises a first light emitting diode and said second source of light comprises a second light emitting diode.

16. Apparatus as set forth in claim 15 wherein said first and second light emitting diodes emit visible light.

17. Apparatus as set forth in claim 14 further comprising:

a third source of light positioned to illuminate a third region of said container;

third means for driving said third source of light at said first frequency;

third photodetector means positioned for receiving light of said third source which illuminates said third region of said container while avoiding light of said first source; and third receiver and demodulator means coupled to said third photodetector means and tuned to said first frequency for extracting inspection information from said third photodetector means.

18. Apparatus as set forth in claim 14 wherein said first photodetector means is positioned to receive light reflected from a check in said first region of said container, and said second photodetector means is positioned to receive light reflected from a check in said second region of said container.

19. A process for inspecting a glass container for defects, said process comprising the steps of:

illuminating a first region of said container with first modulated light, sensing said first modulated light which reflects from a first defect in said first region and generating corresponding first output signals, demodulating said first output signals to detect said first defect, illuminating a second region of said container with second modulated light, sensing said second modulated light which reflects from a second defect in said second region and generating corresponding second output signals, and demodulating said second output signals to detect said second defect in said second region.

* * * * *